United States Patent
Lore et al.

(10) Patent No.: US 10,909,164 B2
(45) Date of Patent: Feb. 2, 2021

(54) METHOD FOR UPDATING AN INDEX OF A PERSON

(71) Applicant: Essilor International, Charenton-le-Pont (FR)

(72) Inventors: Marie Lore, Charenton-le-Pont (FR); Marion Swital, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 170 days.

(21) Appl. No.: 15/562,590

(22) PCT Filed: Apr. 1, 2016

(86) PCT No.: PCT/EP2016/057253
§ 371 (c)(1),
(2) Date: Sep. 28, 2017

(87) PCT Pub. No.: WO2016/156586
PCT Pub. Date: Oct. 6, 2016

(65) Prior Publication Data
US 2018/0107662 A1  Apr. 19, 2018

(30) Foreign Application Priority Data
Apr. 2, 2015 (EP) .................................... 15305496

(51) Int. Cl.
*G06F 16/26* (2019.01)
*G06F 16/435* (2019.01)
(Continued)

(52) U.S. Cl.
CPC .......... *G06F 16/436* (2019.01); *G02C 5/001* (2013.01); *G02C 5/14* (2013.01); *G06F 3/013* (2013.01);
(Continued)

(58) Field of Classification Search
CPC .............. G06Q 30/02; G06Q 30/0248; G06Q 30/0255; G06Q 30/0267; G06Q 30/0269;
(Continued)

(56) References Cited

U.S. PATENT DOCUMENTS 8,488,851 B2 * 7/2013 Artal Soriano ...... A61B 3/1176
351/211
8,499,001 B1 * 7/2013 To .......................... G16B 50/00
707/767

(Continued)

OTHER PUBLICATIONS

International Search Report dated Jul. 14, 2016 in PCT/EP2016/057253.
(Continued)

*Primary Examiner* — Shyue Jiunn Hwa
(74) *Attorney, Agent, or Firm* — Oblon, McClelland, Maier & Neustadt, L.L.P.

(57) ABSTRACT

A method for updating an index of a person, the method includes: an index providing during which an index is defined as a function of at least one parameter related to the person is provided; a parameter monitoring during which the at least one parameter of the person is monitored over time; an index update during which the index of the person is updated based on the evolution over time of the at least one parameter of the person.

15 Claims, 3 Drawing Sheets

S1: Index providing step

S2: Parameter monitoring step

S3: Index update step

(51) Int. Cl.
*G06Q 50/22* (2018.01)
*G02C 5/00* (2006.01)
*G02C 5/14* (2006.01)
*G06F 3/01* (2006.01)
*G06K 9/00* (2006.01)

(52) U.S. Cl.
CPC .......... *G06F 3/015* (2013.01); *G06K 9/0061* (2013.01); *G06K 9/00335* (2013.01); *G06Q 50/22* (2013.01)

(58) Field of Classification Search
CPC ............ G06Q 30/0273; G06Q 10/087; G06Q 30/0601; G06Q 30/0253; G06Q 30/06; G06Q 30/0623; G06Q 30/0633; G06Q 30/0641; G06Q 40/04; G06Q 10/06; G06Q 10/10; G06Q 10/20; G06Q 20/10; G06Q 30/0222; G06Q 30/0261; G06Q 30/0283; G06Q 30/04; G06Q 40/00; G06Q 40/06; G06Q 40/12; G06Q 40/123; G06Q 40/125; G06Q 50/01; G06F 3/048; G06F 11/1438; G06F 11/1441; G06F 16/00; G06F 21/568; G06F 21/575; G06F 3/0481; G06F 3/0482; G06F 9/06; G06F 9/4406; G06F 9/4418; G06F 3/013; G06F 3/011; G06F 3/017; G06F 3/14; G06F 3/147; G06F 11/3419; G06F 11/3438; G06F 11/3485; G06F 16/172; G06F 16/21; G06F 16/22; G06F 16/27; G06F 16/44; G06F 16/71; G06F 16/951; G06F 16/958; G06F 19/00; G06F 1/3228; G06F 1/3265; G06F 21/316; G06F 21/53; G06F 2201/81; G06F 3/012; G06F 3/016; G06F 3/0202; G06F 3/0304; G06F 3/0312; G06F 3/0346; G06F 3/03547; G06F 3/0414; G06F 3/044; G06F 3/045; G06F 3/04817; G06F 3/04842; G06F 3/04845; G06F 3/04847; G06F 9/45529; G06N 20/00; G06N 5/025; G06N 5/022
See application file for complete search history.

(56) References Cited

U.S. PATENT DOCUMENTS

| | | | |
|---|---|---|---|
| 8,971,570 B1 | 3/2015 | Raffle et al. | |
| 2001/0028309 A1* | 10/2001 | Torch | A61B 3/0066 340/575 |
| 2003/0167156 A1* | 9/2003 | Alba | G06F 17/5009 703/2 |
| 2008/0146892 A1 | 6/2008 | Leboeuf et al. | |
| 2011/0098112 A1 | 4/2011 | Leboeuf et al. | |
| 2011/0106627 A1 | 5/2011 | Leboeuf et al. | |
| 2011/0211056 A1 | 9/2011 | Publicover et al. | |
| 2012/0197737 A1 | 8/2012 | Leboeuf et al. | |
| 2012/0203081 A1 | 8/2012 | Leboeuf et al. | |
| 2012/0226111 A1 | 9/2012 | Leboeuf et al. | |
| 2012/0226112 A1 | 9/2012 | Leboeuf et al. | |
| 2014/0275855 A1 | 9/2014 | Leboeuf et al. | |
| 2014/0287833 A1 | 9/2014 | Leboeuf et al. | |
| 2014/0288396 A1 | 9/2014 | Leboeuf et al. | |
| 2015/0141772 A1 | 5/2015 | Leboeuf et al. | |
| 2015/0181100 A1 | 6/2015 | Publicover et al. | |
| 2016/0007888 A1* | 1/2016 | Nieminen | A61B 5/1118 600/595 |
| 2017/0323034 A1* | 11/2017 | Song | G06F 17/5009 |

OTHER PUBLICATIONS

Bradley A. Davis, et al. "Oculus Rift in Action", Manning Publications Co., vol. MEAP Edition, Version 12, XP055195660, 2015, pp. 1-31 (with four cover pages).
"SensoMotoric Instruments", Wikipedia, XP055195574, 2015, pp. 1-4.
"Head-mounted display", Wikipedia, XP055195570, 2015, pp. 1-9.
"Eye tracking", Wikipedia, XP055195571, 2015, pp. 1-15.

* cited by examiner

Fig. 1
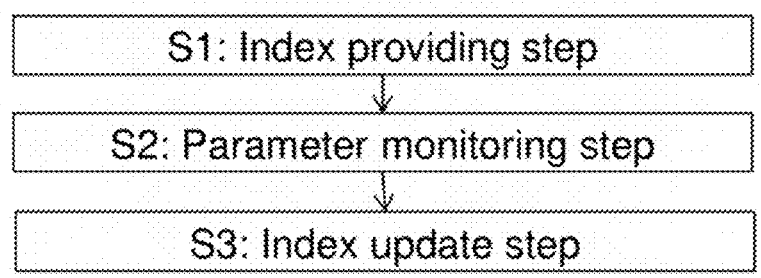
Fig. 2
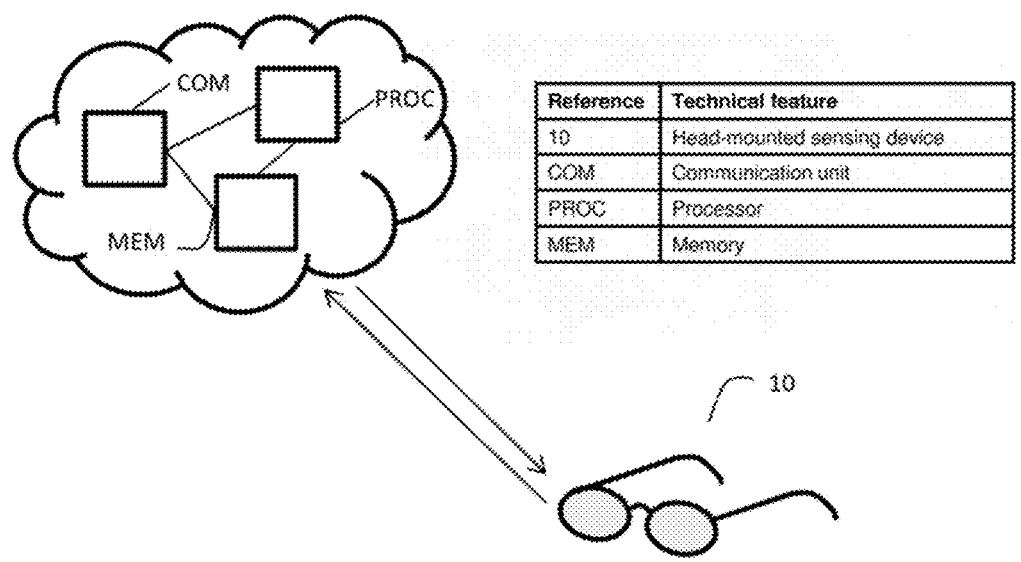
Fig. 4

| Reference | Technical feature |
|---|---|
| 10 | Head-mounted sensing device |
| 12 | Spectacle frame |
| 14 | Communication unit |
| 20, 22, 24 | Cameras |
| 30, 32, 34 | Illumination sources |
| 40, 42 | Sensors |

| Reference | Technical feature |
|---|---|
| 11 | Display source |
| 13 | Collimating device |
| 16 | Optical insert |
| 18 | Output waves |
| 20, 22 | Major surfaces |
| 24 | Reflecting surface |
| 26 | Optical element |

METHOD FOR UPDATING AN INDEX OF A PERSON

FIELD OF THE INVENTION

The invention relates to a method for updating an index of a person, for example a vision capital index of a person. The invention further relates to a mounted sensing device and to a system for updating an index of a person, for example a vision capital index of a person.

BACKGROUND OF THE INVENTION

With the progress of science and statistics, one is able to define index of person or a group of person based on different parameters such as their ages, their place of living or their living habits.

For example, life expectancy of an individual or a group of individual may be estimated based on different parameter such as the year of their birth, their current age and other demographic factors including gender.

However, more personalized parameters may influence the life expectancy of an individual. For example, if such individual has smoking habits, this is known to reduce the life expectancy of such individual.

More and more parameters of an individual are known to have an influence on life expectancy. Furthermore, one may define other index as a function of at least one parameter of an individual.

Therefore, there is a need for a method for updating an index of a person so as to provide to the person an updated index.

One object of the present invention is to provide such a method and a system allowing such update.

SUMMARY OF THE INVENTION

To this end, the invention proposes a method, for example implemented by computer means, for updating an index of a person, the method comprises:
  an index providing step during which an index is defined as a function of at least one parameter related to the person is provided,
  a parameter monitoring step during which the at least one parameter of the person is monitored over time,
  an index update step during which the index of the person is updated based on the evolution over time of the at least one parameter of the person.

Advantageously, the monitoring of a parameter of the person over time allows updating the index of the person so as to provide to the person an accurate and updated value of the index.

Furthermore, the invention may provide an indication to the person of the influence of his behavior or habits on the index.

The method of the invention may help a person be aware of the effect of such or such parameter on his index and may have the person either change his habits or on the contrary amplify such or such behavior or habit.

According to further embodiments which can be considered alone or in combination:
  the index provided during the index providing step is further defined based on at least one addition parameter intrinsic to the person; and/or
  the at least one parameter of the person is a visual behavior parameter relating to the visual behavior of the person; and/or
  the visual behavior parameter of the person relates to the visual effort of the person; and/or
  the visual behavior parameter relates to gazing behavior of the person, such as gazing direction, gazing distances, variation of gazing distances; and/or
  the visual behavior parameter relates to oculomotor parameters of the person, such as eye movements, saccades, accommodation, convergence, fixation, distance of fixation and/or
  the visual behavior parameter relates to ocular parameters of the person, such as opening of the eyelid, pupil diameter, level of tears, blink frequency, duration, strength; and/or
  the index of the person is a function of at least one parameter of the environment of the person and the evolution over time of the at least one parameter of the environment of the person is monitored during the monitoring step and the index of the person is updated based on the evolution over time of the at least one parameter of the environment of the person; and/or
  the parameter of the environment of the person relates to the spectral features and intensity of the light received by the person; and/or
  the parameter of the environment of the person relates to temperature and/or humidity of the environment of the person, the amount and/or the type of allergens and/or pollutants contained in the environment of the person and/or the amount of time spent indoor and outdoor by the person, and/or the place of life of the person and/or the location of the person;
  the index of the person is a function of at least one parameter of the physiology of the person and the evolution over time of the at least one parameter of the physiology of the person is monitored during the monitoring step and the index of the person is updated based on the evolution over time of the at least one parameter of the physiology of the person; and/or
  the parameter of the physiology of the person relates to the ametropia of the person and/or features of the eyes of the person such as eye color, pupil diameter, and/or the age, and/or the height and/or the weight of the person; and/or
  the index of the person is a function of at least one parameter of the life habit of the person and the evolution over time of the at least one parameter of the life habit of the person is monitored during the monitoring step and the index of the person is updated based on the evolution over time of the at least one parameter of the life habit of the person; and/or
  the parameter of the life habit of the person relates to the food habits of the person and/or the tobacco habits of the person and/or the alcohol habits of the person and/or the sleep habits of the person and/or the physical activity habits of the person and/or the rhythm of life of the person and its regularity and/or sunglasses wearing habits of the person and/or the professional life of the person; and/or
  the index of the person is a function of at least one parameter of the health of the person and the evolution over time of the at least one parameter of the health of the person is monitored during the monitoring step and the index of the person is updated based on the evolution over time of the at least one parameter of the health of the person; and/or
  the parameter of the health of the person relates to general health of the person and/or ocular health of the person and/or the treatments of taken by the person the pathologies of the person and/or heart rate of the person, and/or blood oxygenation of the person; and/or
the index relates to a vision capital of the person; and/or
the index relates to a sleep index of the person; and/or
the index of the person is a function of at least one of the bed time, wake/up time, tonicity of the person before sleeping, and turquoise light exposure of the person; and/or
the index relates to an outdoor capital of the person; and/or
the index of the person is a function of at least one of the time spent outdoors, exposure time to UV and/or blue light; and/or
the index relates to a fitness index of the person; and/or
the index of the person is a function of at least one of the activity level, the number of steps, the posture of the person while sitting.

The invention further relates to a mounted sensing device adapted to be worn by a wearer and comprising:
at least one sensor configured to sense at least one parameter of the wearer; and
a communication unit configured to communicate the at least one sensed parameter to a monitoring unit.

According to further embodiments which can be considered alone or in combination:
the mounted sensing device is a head mounted sensing device; and/or
the head mounted device further comprises a spectacle frame, and the at least one sensor is mounted on the spectacle frame; and/or
the head mounted device further comprises an optical lens and the at least one sensor is on or within the optical lens; and/or
the head mounted device further comprises a display unit adapted to display an image to the wearer.

The invention also relates to a system for updating an index of a person comprising:
a communication unit configured to receive an index of a person defined as a function of at least one parameter of the person,
a monitoring unit configured to monitor the at least one parameter of the person over time, and
a processor configured to process at the least one parameter of the person so as to update the at least one index of the person based on the evolution over time of the at least one parameter of the person.

The system for updating an index of a person according to the invention may further comprises a mounted sensing device according to the invention, the monitoring unit being configured to monitor the at least on parameter of the person sensed by the at least one sensor.

According to a further aspect, the invention relates to a system for updating an index of
a person, comprising:
a memory; and
a processor arranged to execute a program instructions stored in the memory to:
receive an index defines as a function of at least one parameter related to the person,
monitor over time at least one parameter of the person,
update the index of the person based on the evolution over time of the at least one parameter of the person.

The invention further relates to a computer program product comprising one or more stored sequences of instructions that are accessible to a processor and which, when executed by the processor, causes the processor to carry out the steps of the method according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which:

FIG. 1 is an illustration of a chart-flow of a monitoring method according to the invention;

FIG. 2 is a table illustrating a function defining an index according to the invention;

FIG. 4 represents a networked data-processing device according to the invention.

DETAILED DESCRIPTION OF PREFERRED EMBODIMENTS

Figure 3:
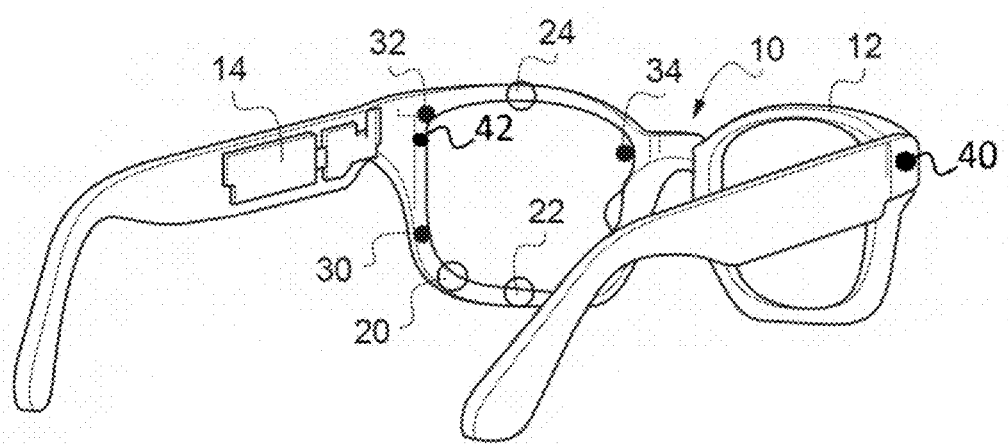
FIG. 3 represents a head mounted sensing device according to the invention.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

As illustrated on FIG. 1, the method for updating an index of a person comprises:
an index providing step S1,
an parameter monitoring step S2,
an index update step S3.

During the index providing step S1, an index defined as a function of at least one parameter related to the person is provided.

The index may relate to a vision capital of a person. The vision capital provides a health estimate of the vision system, the vison quality, and the visual comfort of the person allowing to identify risk factors for the development of vision system diseases or induce premature aging vision.

Many parameters related to the person may be considered when determined a vision capital.

An initial value of the index defined as a function to at least one parameter related to the person is determined and provided during the index providing step.

Many different functions and parameters may be considered to determine the index of the person.

Typically, the index may be express as:
$I=f(P1(t0),P2(t0), \ldots , Pn(t0))$, with f a function of parameters P1, P2 to Pn related to the person.

Among the different parameters P1 to Pn some may change overtime, such as the age or the ametropie of the person and some may remain constant such as the gender of the person.

Among the parameters that change over time one may distinguish between the parameter whose change is predictable, such as the age of the person from the parameter whose change is much more difficult or even impossible to predict, such as the ametropie of the person.

The index may be defined as:
$I=f(g1(P1),g2(P2), \ldots , gn(Pn))$, with gi a function of a parameter Pi related to the person. Typically the function gi may be defined between 0 and 1 based on minimum and maximum values of the parameter Pi. The function f may be a sum, an average, a weighted sum or any other suitable function.

The function gi may be linear between its minimum and maximum values. Furthermore, the function gi may change from one parameter to the other and from one person to the other.

Among the parameters defining the index at least one of the parameter is to be intrinsic to the person.

According to a preferred embodiment of the invention, at least one parameter defining the index relates to the visual behavior of the person.

The visual behavior parameter may relate to the visual effort of the person.

The visual behavior parameter may relate to the gazing behavior of the person, such as such as gazing direction, gazing distances, variation of gazing distances.

The visual behavior parameter may relate to oculomotor parameters of the person, such as eye movements, saccades, accommodation, convergence, fixation, distance of fixation.

For example, the function gi relating to the distance of fixation may be maximum when the person goes through far distance vision for at least 20 second every 20 minutes at near distance vision and minimum when the person passes over 40 minutes gazing at near vision distance without gazing at far vision distance.

Typically, the function gi may be a linear function of the time gazing at far vision distance and the time gazing a near vision distance.

As illustrated in the table of FIG. 2, the function gi varies from 1 when the person goes through far distance vision for at least 20 second every 20 minutes at near distance vision to 0 when the person either does not take any break gazing at far vision distance or spends more than 40 minutes gazing at near vision distance before taking a break gazing at far vision distance.

The function gi relating to the saccades may be maximum when the saccades are ordered while reading and may be minimum when they are disordered and unexpected.

The function gi relating to the fixation may be maximum when the fixation is fluid and steady and minimum when the fixation is inaccurate.

The function gi relating to the convergence may be maximum when the ratio accommodation versus convergence is close to 1 and minimum when the ratio accommodation versus convergence is either too high or too low.

The visual behavior parameter may relate to ocular parameters of the person, such as opening of the eyelid, pupil diameter, level of tears, blink frequency, duration, strength, the lacrimal layer, the appearance of the ocular surface.

The function gi relating to the level of tears may be maximum when the lachrymal prism is greater than 0.4 mm and minimum when the lachrymal prism is smaller than 0.2 mm.

The function gi relating to the lacrimal layer may be maximum when the thickness of the lacrimal layer is greater than 20 nm and minimum when the thickness of the lachrymal prism is smaller than 20 nm.

The function gi relating to the level of tears may be maximum when corresponding to the zero level of the Efron scale and minimum when corresponding to a level greater than 2 on the Efron scale. Typically, the function gi is a linear function between its maximum and minimum. Another scale than the Efron scale may be used with a different gi function.

The function gi relating to the opening of the eyelid may be maximum when stable over time and minimum when unstable over time.

The function gi relating to the pupil diameter may be maximum when light reflex, accommodative reflex and a symmetric response of the pupil relative to each other is observed and minimum when malfunction of the pupillary light reflex or accommodative or dissymmetry is observed.

The function gi relating to the frequency and/or force and/or length of blink may be maximum when such parameters are stable over the day and minimum when such parameters have important variation over time.

The visual behavior parameter may relate to the ametropia of the person, such as the value of ametropia, accuracy of the optical correction, evolution of ametropia, appropriate use of optical lenses, use of contact lenses, appropriate use of contact lenses.

The function gi relating to the value of ametropia may be maximum when smaller than −6D for myopia and greater than 4D for farsighted and minimum otherwise.

The function gi relating to the accuracy of the optical correction may be maximum when the optical correction is accurate and minimum when the prescription is 0.5D over of below the accurate optical correction.

The function gi relating to the evolution of ametropia may be maximum when the ametropia is stable after 20 years old and minimum when the ametropia changes after 25 years old.

The function gi relating to the appropriate use of optical lenses may be maximum when the use of optical lens is adapted and minimum when the use of optical lenses is not adapted.

The function gi relating to the use of contact lenses may be maximum when the no contact lenses are used and minimum when the person uses contact lenses on a regular base.

The function gi relating to the appropriate use of contact lenses may be maximum when the contact lenses are adapted to the person, are changed regularly, and properly maintained and minimum otherwise.

The visual behavior parameter may relate to the vision activity of the person, such as the time spent gazing at near vision, the time spent gazing at a screen, the time spend gazing at a virtual environment, the time spent gazing at increased reality, the time spend in low luminosity.

The function gi relating to the time spent gazing at near vision may be maximum when such time is smaller than 3 hours a day and minimum when such time is greater than 6 hours a day.

The function gi relating to the time spent gazing at a screen may be maximum when such time is smaller than 2 hours a day and minimum when such time is greater than 6 hours a day.

The function gi relating to the time spent gazing at a virtual environment may be maximum when such time is smaller than 3 hours a week and minimum when such time is greater than 6 hours a week.

The function gi relating to the time spent gazing at increased reality may be maximum when such time is smaller than 3 hours a day and minimum when such time is greater than 8 hours a day.

The function gi relating to the time spent in low luminosity may be maximum when such time is smaller than 3 hours a day and minimum when such time is greater than 6 hours a day.

The visual behavior parameter may relate to the vision comfort of the person, such as the eyestrain, blurred vision, difficult visual transition, and double vision.

The function gi relating to the eyestrain, the blurred vision, difficult visual transition, and double vision may be maximum when not occurring and minimum when occurring.

According to an embodiment of the invention, the index of the person is a function of at least one parameter of the environment of the person and the evolution over time of the at least one parameter of the environment of the person.

Among the environment parameter, the spectral features and intensity of the light received by the person may be considered.

The function gi relating to the spectral features may be maximum when such the reception of UV, IR and harmful blue light is limited and minimum when the reception of UV, IR and harmful blue light is important.

The function gi relating to the spectral features may be maximum when the eyes of the person are not exposed to bright light and may be minimum when exposed to bright light.

The parameter of the environment of the person relates to temperature and/or humidity of the environment of the person, the amount and/or the type of allergens and/or pollutants contained in the environment of the person and/or the amount of time spent indoor and outdoor by the person, and/or the place of life of the person and/or the location of the person upon monitoring the index.

The function gi relating to the quality of the environment may be maximum when the environment of the person does not comprise allergens and/or pollutants and may be minimum when the environment of the wearer comprises allergens and/or pollutants.

According to an embodiment of the invention, the index of the person is a function of at least one parameter of the physiology of the person and the evolution over time of the at least one parameter of the physiology of the person is monitored during the monitoring step and the index of the person is updated based on the evolution over time of the at least one parameter of the physiology of the person.

Typically, the parameter of the physiology of the person may relate to the features of the eyes of the person such as eye color, and/or the age, and/or the height and/or the weight of the person.

The index of the person may be function of the activities carried out by the person, such as sport, profession, and hobby.

The function gi relating to the practice of sport, the profession, and hobbies may be minimum when the person practices non-risky sports, has a non-risky profession or non-risky hobbies or carries them out with protective goggles.

According to an embodiment of the invention, the index of the person is a function of at least one parameter of the health of the person.

For example, the parameter of the health of the person relates to general health of the person and/or ocular health of the person, the treatments of taken by the person the pathologies of the person.

According to an embodiment of the invention the index of the person is a function of at least one parameter of the life habit of the person.

For example, the parameter of the life habit of the person relates to the food habits of the person and/or the tobacco habits of the person and/or the alcohol habits of the person and/or the sleep habits of the person and/or the physical activity habits of the person and/or the rhythm of life of the person and its regularity and/or sunglasses wearing habits of the person and/or the professional life of the person.

The function gi relating to the diet of the person may be maximum when the diet is balanced and minimum when the diet comprises many fat and sugar.

The function gi relating to smoking may be maximum when the person is nonsmoking and minimum when the person smokes regularly.

The function gi relating to alcohol use may be maximum when the person drinks least than a glass of win a day and minimum when the person drinks on a regular bases.

The gi relating to coffee use may be maximum when the person drinks least than 5 cups of coffee a day and minimum when the person drinks more than 5 cups of coffee a day.

During the parameter monitoring step S2, at least part of the parameters that may vary with time is monitored over time.

Such monitoring may comprise recording on a regular base value of the parameter and calculating the value of the gi function based on the adjusted value.

The parameters may be provided by a sensing device, such as a head mounted device equipped with sensors, and/or directly by the person itself, and/or from a data base and/or lookup table.

The index is updated during the index update step S3 based on the evolution over time of the at least one parameter of the person. Typically a new value of the function f is determined based either on the new value of the parameter or on the new values of the gi function.

The index, in particular the visual capital of the person may be increased based on further elements, such as the use of dietary supplement or decreased based on the fact that the person as a specific diseases or health condition.

According to an embodiment of the invention, the index may relate to a sleep index of the person. For example, the index of the person may be a function of at least one of the bed time, wake/up time, tonicity of the person before sleeping, and turquoise light exposure of the person.

The turquoise part of the light spectrum has an impact on circadian rhythm and then on bedtime and sleep quality.

According to an embodiment of the invention, the index may relate to an outdoor capital of the person. For example, the index of the person may be a function of at least one of the time spent outdoors, exposure time to UV and/or blue light.

The blue-violet light exposure can be toxic for retinal cells and is a risk factor for AMD.

In the sense of the invention blue light and turquoise light correspond to wave lengths comprised between 380 and 520 nm.

The invention further relates to a mounted sensing device adapted to be worn by a wearer and comprising:
at least one sensor configured to sense at least one parameter of the wearer; and
a communication unit configured to communicate the at least one sensed parameter to a monitoring unit.

Typically, the mounted sensing device is a head mounted sensing device.

An example of head mounted sensing device is illustrated on FIG. 3. The head mounted sensing device 10 represented on FIG. 3 comprises a spectacle frame 12 with three cameras 20, 22, 24 directed at the left eye (not shown) of the wearer. The cameras 20, 22, 24 are arranged to be directed toward the head in order to track the locations of the eyes of the wearer and/or the structures of the eyes of the wearer, for example the pupils, eyelids, irises, glints, and/or other reference points in the region of the eye(s).

The cameras 20, 22, 24 may include charge-coupled device (CCD), complementary metal-oxide-semiconductor (CMOS), or other photodetectors that include an active area, e.g., including a rectangular or linear or other array of pixels, for capturing images and/or generating video signals representing the images. The active area of each of the cameras 20, 22, 24 may have any desired shape, e.g., a square or rectangular shape, circular, and the like. The surface of the active area of one or more cameras may also be curved, if desired, e.g., to compensate during image acquisition for the nearby three-dimensional curvature of the eye and surrounding structures being imaged.

The head mounted sensing device 10 further comprises three illumination sources 30, 32, 34 arranged so as to illuminate the left eye of the wearer when wearing the spectacle frame 12.

The three illumination sources 30, 32, 34 are fixed to the spectacle frame 12. In an exemplary embodiment, illumination sources 30, 32, 34 may include light-emitting diodes (LEDs), organic LEDs (OLEDs), laser diodes, or other devices that convert electrical energy into photons. Each illumination source 30, 32, 34 may be used to illuminate the eye to acquire images using any of the cameras 20, 22, 24 and/or to produce reference glints for measurement purposes to improve gaze-tracking accuracy. In an exemplary embodiment, each light source 30, 32, 34 may be configured for emitting a relatively narrow or wide bandwidth of the light, for example infrared light at one or more wavelengths between about 700-1000 nanometers. For example, AlGaAs LEDs provides an emission peak at 850 nm and are widely used and affordable, while commodity CMOS cameras used in mobile phones and webcams show a good sensibility at this wavelength.

The head mounted sensing device 10 further comprises a communication unit 14 configures to communicate data indicative of the visual behavior if the user of the head mounted device to a comparison unit.

Although not represented, the eye tracking device further comprises a power source, for example a battery and/or other electronics. Advantageously, the power source and/or other electronics may be arranged on the same side of the spectacle frame than the communication unit 14 so as to facilitate the integration of the electronics devices on the spectacle frame.

Although on FIG. 3 cameras and illumination sources have been represented only on the left side of the spectacle frame, the sensor may very well comprise cameras and illumination sources and/or on the right side of the spectacle frame.

Advantageously, having cameras on both sides of the spectacle frame allows providing accurate information on the gazing direction and distance of the wearer.

For example, such eye tracking device can be used for long periods of time so as to determine accurately in everyday life conditions the visual behavior of the wearer.

Furthermore, although on FIG. 3, the sensors have been represented on the spectacle frame, such sensors may be on or within the optical lenses.

Although the mounted sensing device has been described with eye trackers, the mounted sensing device may comprise other type of sensors, such as photodiodes.

As represented on FIG. 3, the mounted sensing device may comprise a sensor 40 configured to sense environment parameters and/or a sensor configured to sense ocular parameters of the eye of the wearer such as blink frequency, and/or an sensor, not represented, on the bridge of the spectacle frame facing in front of the wearer of the frame configured to measure the gazing distance, and/or a sensor configure to measure the luminosity of the environment.

The monitoring of a visual behavior parameter of the user of the mounted device requires having the communication unit 14 configured to communicate data indicative of the at least senses parameter a monitoring unit.

The monitoring unit is typically included in a system for monitoring the visual behavior. Such system may comprises:
a communication unit configured to receive an index of a person defined as a function of at least one parameter of the person,
a monitoring unit configured to monitor the at least one parameter of the person over time, and
a processor configured to process at the least one parameter of the person so as to update the at least one index of the person based on the evolution over time of the at least one parameter of the person.

The monitoring system may be integrated in the head mounted sensing device so as to have an embedded system.

According to an embodiment of the invention, illustrated on FIG. 4, the head mounted device communicates with a distant entity that comprises a monitoring system. Communication can be done through different communication devices and protocols, like Bluetooth, Zigbee, WiFi or others.

For example, the communication unit is configured to communicate with the distance entity either to store the measured features in a memory MEM or to provide an information indicative of the visual behavior of the head mounted device and the user of the head mounted device.

Typically, the distance entity comprises a communication unit COM configured to communicate at least with the head mounted device, a memory MEM, at least one processor PROC and program instructions stored on a non-transitory computer-readable medium and executable by the at least one processor to execute the step of the monitoring method of the invention.

The distance entity can include different computing objects such as personal digital assistants, audio/video devices, mobile phones, MPEG-1 Audio Layer 3 (MP3) players, personal computers, laptops, tablets, bluetooth headset, watch, wristband, etc. . . . .

The monitoring unit may be configured to receive data from a distant sensing device, such as a head mounted sensing device, and/or directly from the person itself and/or from a data base or look-up table. Each computing object and the head mounted device can communicate with one or more other by way of a communication network, either directly or indirectly. Even though illustrated as a single element in FIG. 4, network can include other computing objects and computing devices that provide services to the system of FIG. 4, and/or can represent multiple interconnected networks, which are not shown.

In a network environment in which the communications network/bus can be the Internet, the computing objects can be Web servers, file servers, media servers, etc. with which the client computing objects or devices communicate via any of a number of known protocols, such as the hypertext transfer protocol (HTTP).

The head mounted device according to the invention may comprise a virtual image display device, preferably allowing the wearer to see both the virtual image and the real world through it. The virtual image display device is able to display graphical images, and an electronic driving system (memory+processor) sends to the virtual display image the image to display. Preferably it is able to display image in different viewing directions, and this displaying direction and the position of the field of view, can be adapted from the relative position measured by the sensors. Furthermore, the image to be displayed can be modified depending of the visual behavior measured by the sensors.

Information concerning the monitoring of the index of the person may be provided to the person or a third party as visual indications and/or audio indications, and/or tactile indications such as vibrations.

Figure 5:
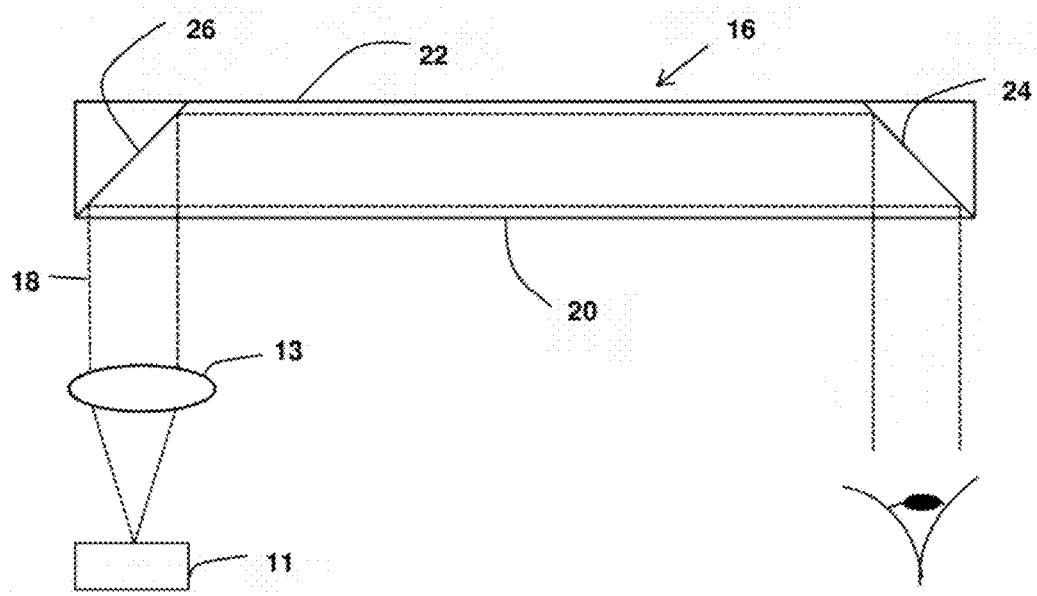
FIG. 5 is a schematic representation of a head mounted sensing device according to a further embodiment of the invention.

An example of see-through display system is illustrated in FIG. 5. Such see-trough display system comprises a display source 11, a collimating device 13, and an optical insert 16 constituted by a light-guide optical element 16 (LOE).

The display source 11 can be emissive or not emissive.

The light-guide optical element 16 typically includes at least two major surfaces 20 and 22 and edges, at least one partially reflecting surface 24 and an optical element 26 for coupling light thereinto. The output waves 18 from the collimating device 13 enter the light-guide optical element 16 through its lower surface 20. The incoming waves (towards the light-guide optical element 16) are reflected from the surface 26 and trapped in the light-guide optical element 16.

In an embodiment, the electro-optical system may comprise a plane light-guide optical element 16 with at least two planes major surfaces 20 and 22. For example, such a light guide optical element 16 may be one of Lumus Company.

In an alternative embodiment, the electro-optical system may comprise a curved light-guide optical element 16.

The light-guide may be encapsulated in an optical lens or placed in front of an optical lens.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims. In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for updating an index of a person, the method comprises:
   obtaining the index of the person, which is defined as a function of at least one life parameter of the person;
   monitoring the at least one life parameter of the person over time;
   updating the index of the person based on evolution over time of the at least one life parameter of the person,
   wherein the index of the person corresponds to a vision capital of the person, the vision capital providing an indication of eye health of the person and the at least one life parameter of the person is a visual behavior parameter relating to visual behavior of the person, the visual behavior parameter of the person relating to a visual effort of the person.

2. The method according to claim 1, wherein the index obtained during the index obtaining is further defined based on at least an additional parameter intrinsic to the person.

3. The method according to claim 1, wherein the index of the person is a function of at least one parameter of environment of the person, and evolution over time of the at least one parameter of the environment of the person is monitored during the monitoring, and the index of the person is updated based on the evolution over time of the at least one parameter of the environment of the person.

4. The method according to claim 3, wherein the parameter of the environment of the person relates to spectral features and intensity of light received by the person.

5. The method according to claim 1, wherein the index of the person is a function of at least one parameter of physiology of the person, and evolution over time of the at least one parameter of the physiology of the person is monitored during the monitoring, and the index of the person is updated based on the evolution over time of the at least one parameter of the physiology of the person.

6. The method according to claim 1, wherein the index of the person is a function of at least one parameter of life habit of the person, and evolution over time of the at least one parameter of the life habit of the person is monitored during the monitoring, and the index of the person is updated based on the evolution over time of the at least one parameter of the life habit of the person.

7. The method according to claim 1, wherein the index of the person is a function of at least one parameter of health of the person, and evolution over time of the at least one parameter of the health of the person is monitored during the monitoring, and the index of the person is updated based on the evolution over time of the at least one parameter of the health of the person.

8. The method according to claim 1, wherein the index relates to a sleep index of the person.

9. The method according to claim 8, wherein the index of the person is a function of at least one of the bed time, wake/up time, tonicity of the person before sleeping, and turquoise light exposure of the person.

10. The method according to claim 1, wherein the index relates to an outdoor capital of the person.

11. The method according to claim 10, wherein the index of the person is a function of at least one of the time spent outdoors, exposure time to ultraviolet and blue light.

12. The method according to claim 1, wherein the index relates to a fitness index of the person.

13. The method according to claim 12, wherein the index of the person is a function of at least one of activity level, number of steps, posture of the person while sitting.

14. A system for updating an index of a person comprising:
processing circuitry configured to
receive the index of the person defined as a function of at least one life parameter of the person,
mind
monitor the at least one life parameter of the person over time, and
process at the least one life parameter of the person to update the at least one index of the person based on evolution over time of the at least one life parameter of the person,
wherein the index of the person corresponds to a vision capital of the person, the vision capital providing an indication of eye health of the person and the at least one life parameter of the person is a visual behavior parameter relating to visual behavior of the person, the visual behavior parameter of the person relating to a visual effort of the person.

15. The system according to claim 14, wherein the system further comprises a mounted sensing device configured to monitor the at least one life parameter of the person sensed by at least one sensor.

* * * * *